United States Patent
Vachon

[11] Patent Number: 6,038,482
[45] Date of Patent: Mar. 14, 2000

[54] OPEN BORE ELECTRODE WITH A TIERED DRUG THERAPY DELIVERY SYSTEM

[75] Inventor: David J. Vachon, Granada Hills, Calif.

[73] Assignee: Pacesetter, Inc., Sylmar, Calif.

[21] Appl. No.: 09/183,012

[22] Filed: Oct. 30, 1998

[51] Int. Cl.$^7$ ................................ A61N 1/05
[52] U.S. Cl. ........................................ 607/120
[58] Field of Search ............................ 607/115, 116, 607/119, 120

[56] References Cited

U.S. PATENT DOCUMENTS

| | | | |
|---|---|---|---|
| 3,923,060 | 12/1975 | Ellinwood, Jr. | 128/260 |
| 4,003,379 | 1/1977 | Ellinwood, Jr. | 128/260 |
| 4,146,029 | 3/1979 | Ellinweed, Jr. | 128/260 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,711,251 | 12/1987 | Stokes | 128/784 |
| 4,819,661 | 4/1989 | Heil, Jr. et al. | 128/786 |
| 4,819,662 | 4/1989 | Heil, Jr. et al. | 128/786 |
| 4,844,099 | 7/1989 | Skalsky et al. | 128/785 |
| 4,922,926 | 5/1990 | Hirschberg et al. | 128/785 |
| 4,953,564 | 9/1990 | Berthelsen | 128/784 |
| 4,972,848 | 11/1990 | Di Domenico et al. | 128/785 |
| 5,103,837 | 4/1992 | Weidlich et al. | 128/784 |
| 5,447,533 | 9/1995 | Vachon et al. | 607/120 |
| 5,496,360 | 3/1996 | Hoffman et al. | 607/120 |
| 5,531,780 | 7/1996 | Vachon | 607/120 |
| 5,634,899 | 6/1997 | Shapland et al. | 604/51 |

OTHER PUBLICATIONS

US Statutory Invention Registration No. H356, Published Nov. 3, 1987, Stokes et al., US Class: 128/785, Filed Feb. 27, 1985.

*Primary Examiner*—Scott M. Getzow

[57] ABSTRACT

An implantable cardiac stimulation lead comprises an elongated electrical conductor with an electrode configured to deliver a tiered level of drug therapy to a patient. An insulative electrical sheath covers the electrical conductor and an electrical connector is coupled to the proximal end of the electrical conductor, adapted for connection with the pulse generator. An electrically conductive electrode is located at a distal end of the electrical conductor whose proximal end is adapted for connection to an implantable stimulation device, the electrode having an interior cavity and an axial bore extending between an exterior surface and the interior cavity. A matrix member, preferably composed of silicon rubber, is received within the interior cavity and contains a therapeutic drug. The exterior surface is coated and the bore is filled with a therapeutic drug-hydrophilic wetting agent compound and the bore is filled with a wetting agent compounded with the therapeutic drug such that tiered delivery to a recipient of the therapeutic drug is achieved first from the exterior electrode surface, then from the bore, and finally from the matrix member. The opening of the bore at the exterior surface of the electrode is between about 0.1% and 50% of the entire surface area of the electrode and is insufficient to allow the intrusion of body fluid from the recipient into the cavity in the absence of a wetting agent, a hydrophilic, water soluble, biocompatible polymer. The diameter of the bore is between about 0.001 inches and 0.035 inches.

14 Claims, 2 Drawing Sheets

OPEN BORE ELECTRODE WITH A TIERED DRUG THERAPY DELIVERY SYSTEM

FIELD OF THE INVENTION

The present invention relates generally to implantable cardiac electrodes in general, and more particularly to such electrodes having means for controllably releasing a therapeutic drug at the site of implantation of the electrode.

BACKGROUND OF THE INVENTION

Electrical stimulation of the body for medical purposes is well known in the prior art. An example of a device for this purpose is the well-known cardiac pacemaker. In the pacemaker context, as well as other body stimulation contexts, the stimulation is delivered to the desired body site by an electrode carrying lead.

Interactions between the lead and body can vitiate the desired effects of the stimulation. For example, material reactions and healing may encourage fibrosis. In the pacemaking context, fibrosis is believed to be a major factor in the increase in chronic stimulation threshold that is usually experienced. Also, mechanical trauma may result in inflammation of the tissue to be stimulated. Such inflammation may alter the response of the tissue to the stimulation energy, both acutely and chronically.

Other interactions between the lead and body, while not directly affecting the response of the tissue to the stimulation energy, can result in the occurrence of undesirable events. For example, the placement of a pacemaking lead may induce a cardiac arrhythmia. Furthermore, the presence of the lead may also promote thrombus formation.

The interactions noted above have long been recognized and efforts made to ameliorate their consequences. For example, the lead may be configured to reduce mechanical trauma and the response of irritable tissue during lead placement. Materials may be selected for the lead body and electrodes to minimize fibrosis. However, lead configuration must take into account, other factors such as the efficiency of the delivery of the stimulation energy, the ease of lead placement, maintenance of the desired electrode position and reliability of the lead over extended period, of time. An accommodation of these interests has resulted in leads whose configuration necessarily results in undesirable interactions between the lead and body.

The use of therapeutic drugs released in vivo to counter trauma caused by an implanted device such as a cardiac pacemaker lead is well known. Such trauma typically occurs in the region of in which the distal end of the pacing lead contacts the cardiac tissue.

Tined pacing leads which have a cavity or collar at the distal end of the lead containing a drug to counter undesirable interactions between the lead and tissue are disclosed in U.S. Pat. Nos. 4,711,251 and 4,506,680 to Stokes; U.S. Pat. No. 4,844,099 to Skalsky et al.; and U.S. Pat. No. 4,972,848 to Di Domenico et al. Di Domenico et al. Discloses a drug compounded within a polymer matrix which is specifically chosen to be dimensionally stable, not expanding when hydrated. They suggest that the degree of crosslinking of the polymer may be useful in varying the elution rate. The Stokes '680 patent teaches a porous electrode design that houses a plug of swellable material containing a drug.

Steroid-eluting leads having a tip electrode housing a variety of matrix materials with a drug being stored in, and dispensed from, the tip electrode, are disclosed in U.S. Pat. No. 4,819,662 to Heil, Jr. et al.; in U.S. Pat. No. 4,606,118 to Cannon et al.; and in U.S. Pat. No. 4,577,642 to Stokes.

A screw-in pacemaker lead is disclosed in U.S. Pat. No. 4,819,661 to Heil, Jr. et al., which has a chamber open to the distal end of the lead. A matrix impregnated with a therapeutic drug is retained in the chamber. A screw-in lead with a drug impregnated matrix is disclosed in U.S. Pat. No. 4,953,564 to Berthelson in which the drug elutes out by means of a porous sintered elution path. Because the matrix swells in use, an expansion space is provided.

An implantable, porous stimulating electrode with a thin coating of hydrophilic polymer in which is embedded an anti-inflammatory steroid is disclosed in U.S. Pat. No. 5,103,837 to Weidlich. In this system, the steroid simply diffuses from the polymeric layer into the adjoining tissue to reduce growth of connective tissue.

U.S. Pat. No. 4,711,251 to Stokes, mentioned above, includes an embodiment that uses an osmotic pump to control dispensing of the drug. It has two chambers separated from each other by an impermeable membrane. The inner chamber contains the drug and is adjacent the electrode; the outer chamber is separated from body fluids by a semi-permeable membrane. According to the specification, body fluids will enter the outer chamber through the semi-permeable membrane to impart a pressure on the inner chamber via the impermeable membrane, resulting in dispensing of the drug stored within the inner chamber through the electrode. However, it is unclear why body fluids would enter the outer chamber to the extent that pressure would be imparted to the inner chamber. Stokes does not describe anything within the outer chamber that would draw in fluid. A figure shows a fluid in the outer chamber; presumably, this is body fluid which has entered the outer chamber after implantation, since no other outer chamber fluid is mentioned.

U.S. Pat. No. 5,496,360 to Hoffmann et al. describes an electrode that contains at least two matrix devices. One has a principal function of drawing in body fluid, the other has the function of releasing a drug like a steroid, for example, dexamethasone sodium phosphate. This patent presents a concept that may not work. The size of the bore and the electrode porosity are not defined and, therefore, more likely than not, the surface tension of body fluid/water across the opening/open bore, as illustrated will restrict access as a bubble forms. This typically occurs with solid electrodes containing a single opening. Further, the Hoffmann et al. electrode would be very expensive to fabricate. In contrast, the electrode of the present invention is extremely easy to machine and assemble and very cost effective by comparison.

It was with knowledge of the foregoing state of the technology that the present invention has been conceived and is now reduced to practice.

SUMMARY OF THE INVENTION

The present invention relates to an implantable cardiac stimulation device which comprises an electrical pulse generator and an elongated electrical conductor having proximal and distal ends. An insulative electrical sheath covers the electrical conductor and an electrical connector is coupled to the proximal end of the electrical conductor, adapted for connection with the pulse generator. An electrically conductive electrode is located at a distal end of the electrical conductor whose proximal end is connected to the electrical pulse generator, the electrode having a smooth exterior surface, an interior cavity, and an axial bore extending between the exterior surface and the interior cavity. A matrix member, preferably composed of silicon rubber, is received within the interior cavity and contains a therapeutic composition. The exterior surface of the electrode is coated with a hydrophilic wetting agent and the bore is likewise filled with a hydrophilic wetting agent compounded with the therapeutic composition such that tiered delivery to a recipient of the therapeutic composition is achieved first from the exterior electrode surface, then from the bore, and finally from the matrix member. The opening of the bore at the exterior surface of the electrode is between about 0.1% and 50% of the entire surface area of the electrode and is insufficient to allow the intrusion of body fluid from the recipient into the cavity in the absence of a wetting agent, a hydrophilic, water soluble, biocompatible polymer. The diameter of the bore is between about 0.001 inches and 0.035 inches.

According to the invention, at least one cylindrical passage, or bore, extends from the outer electrode surface to the inner cavity housing the drug delivery device. The porosity of the electrode of the invention is at least 0.1% but not exceeding 50%. Furthermore, the percentage of surface area occupied by the bore opening is at least 0.1% but not exceeding 50%. Ideally, the bore occupies between about 0.4% and 10% of the electrode's surface area. The open bore is not sufficiently porous to allow the drug contained within the electrode to be dispensed without the aid of a wetting agent which is loaded within the aforementioned cylindrical bore. The wetting agent is comprised of at least one element which is a hydrophilic, water soluble, biocompatible polymer such as polyethylene glycol (PEG), polyvinyl alcohol (PVA) or simple carbohydrate such as mannose, dextrose or sucrose. There are many other examples of materials that may be used for the application. The key element is the processability of the material as related to getting it into the bore (see cross-sectional diagram). Thus, the single open channel/bore is not sufficiently porous to allow the intrusion of body fluid into the cavity to dissolve the drug and allow the drug to diffuse out to the implant site without the addition of the wetting agent. Furthermore, the wetting agent may be compounded with a therapeutic to allow the delivery of the active agent immediately following implant. When this approach is used, the delivery of drug is tiered. One major advantage of this approach is the relatively small cost of manufacturing such a component. Indeed, the minimal expense of fabricating an electrode with superior characteristics is a primary advantage of the present invention.

A primary feature, then, of the present invention is the provision of an implantable cardiac electrode having provision for controllably releasing a therapeutic drug at the site of implantation of the electrode.

Another feature of the present invention is the provision of such an electrode which can be readily manufactured from commonly available materials.

Still another feature of the present invention is the provision of such an electrode which can be inexpensively manufactured while maintaining the performance achieved by much more expensive electrode designs.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
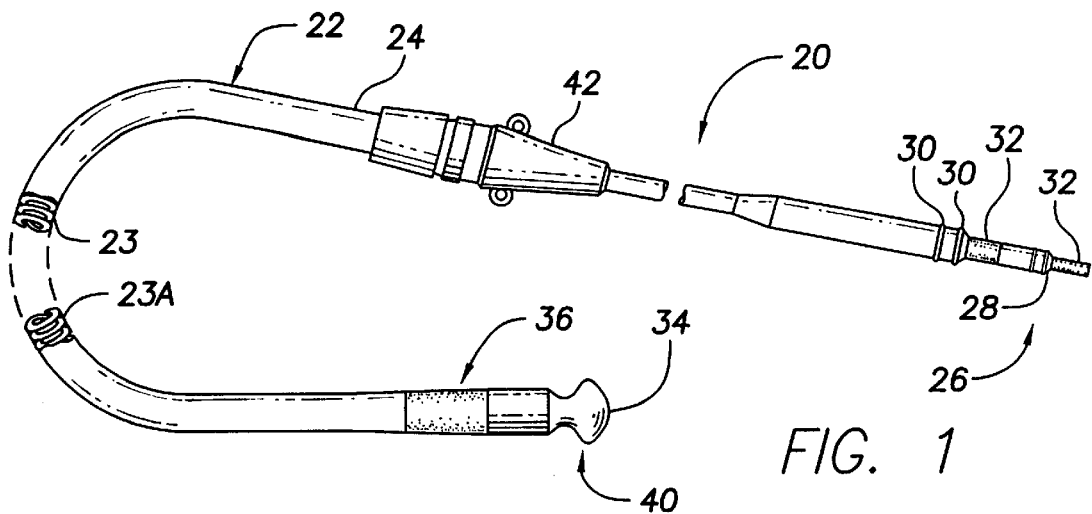
FIG. 1 is a side elevation view of a pacing lead terminating at an electrode embodying the present invention.

Turn now to the drawings and, initially to FIG. 1 which generally illustrates an electrical lead 20 embodying the present invention. The lead 20 may be of the type designed for intravenous insertion for contact with the endocardium, and as such may be conventionally referred to as an endocardial lead. However, the invention need not be so limited. The lead 20 is provided with an elongated lead body 22 which includes coil or helically wound electrical conductors 23, 23A covered with an insulation sheath 24. The insulation sheath is preferably fabricated of silicone rubber, polyurethane, or other suitable material. At a proximal end 26 of the pacing lead 20 is a connector assembly 28, which is provided with sealing rings 30, and which carries at least one, and preferably a couple of electrical connectors 32. The lead 20 extends from the proximal end 26 to a distal end 34 which includes an electrode assembly 36 A fixation sleeve 42 is typically slidably mounted around the lead body 22 to stabilize the pacing lead 20 at the site of venous insertion.

Figure 2:
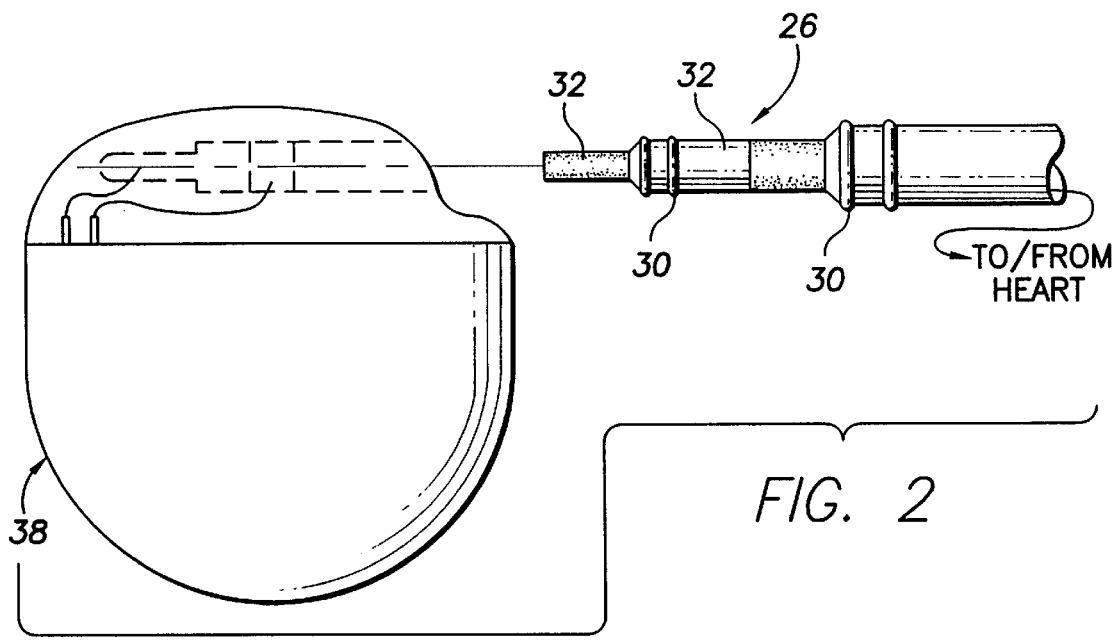
FIG. 2 is an exploded detail side elevation view depicting a proximal end of the lead illustrated in FIG. 1 about to be connected with a pulse generator in the form of a pacemaker.

The connector assembly 28 at the proximal $2^{nd}$ 26 of the electrical lead 20 is adapted for connection with a pulse generator illustrated in FIG. 2 as a pacemaker 38. By means of the conductors 23, 23A, an electrically conductive electrode 40, a component of the electrode assembly 36 at the distal end 34 of the lead 20, is connected to the electrical pulse generator 38. The electrode 40 has an exterior surface 42, an interior cavity 44, and an axial bore 46 extending between the exterior surface and the interior cavity.

A matrix member 48, preferably composed of silicone rubber but of any other suitable material, is received within the interior cavity 44 and contains a therapeutic drug such as dexamethasone sodium phosphate. The exterior surface 42 of the electrode 40 is coated with a wetting agent compounded with the therapeutic drug 50. The wetting agent is comprised of at least one element which is a hydrophilic, water soluble, biocompatible material such as polyethylene glycol (PEG), polyvinyl alcohol (PVA) or simple carbohydrate such as mannose, dextrose or sucrose. There are many other examples of materials that may be used for this purpose. Further, the same therapeutic drug (such as dexamethasone sodium phosphate) as contained in the matrix member 48 would be compounded with the wetting agent. In a similar manner, the bore 46 is filled with a wetting agent compounded with the therapeutic drug. While many different materials may be successfully used for this purpose, it will be appreciated, that there must be consistency of material usage for a single electrode 40.

With this construction, tiered delivery of the therapeutic drug to a recipient of the electrical lead 20 is achieved, first from the exterior electrode surface 42, then from the bore 46, and finally from the matrix member 48. The therapeutic drug elutes from the exterior surface 42 immediately then, together with that contained within the bore 46 over approximately a 24-hour period, then that contained by the matrix member 48 continues to elute for a much longer term measured in months and years.

The diameter of the bore 46 must be insufficient to allow the intrusion of body fluid from the recipient into the cavity in the absence of a wetting agent. An elemental in vitro laboratory test for determining the adequacy of the wetting agent is whether or not an entrapped air bubble or air pocket forms at the entrance to the bore at the exterior surface 42. The formation of an entrapped air bubble or pocket is a clear indication that there is no, or an inadequate amount, of wetting agent.

Experimentation has determined that the porosity of the exterior surface 42 and of the bore 46 must be at least about 0.1% and no greater than about 50%. Spoken in a different way, the opening of the bore 46 at the exterior surface of the electrode must be between about 0.1% and 50% of the entire surface area of the electrode. In making this statement in still a different way, the diameter of the bore 46 must be between about 0.001 inches and 0.025 inches.

A test of an implantable lead having an electrode which delivers an anti-inflammatory or other therapeutic in a tiered fashion, all in the manner of the present invention will now be described in the following example.

EXAMPLE

Figure 3:
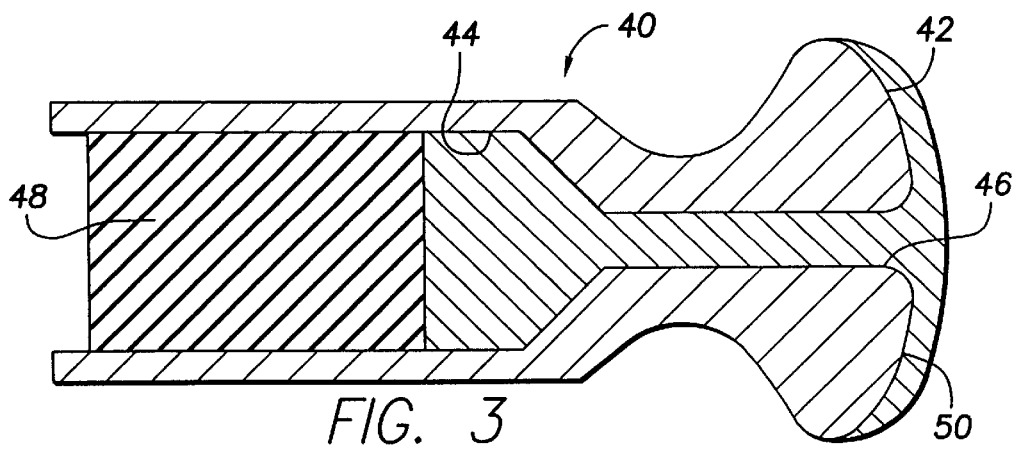
FIG. 3 is a detail side elevation view, in section, illustrating the electrode of the invention.
Figure 4:
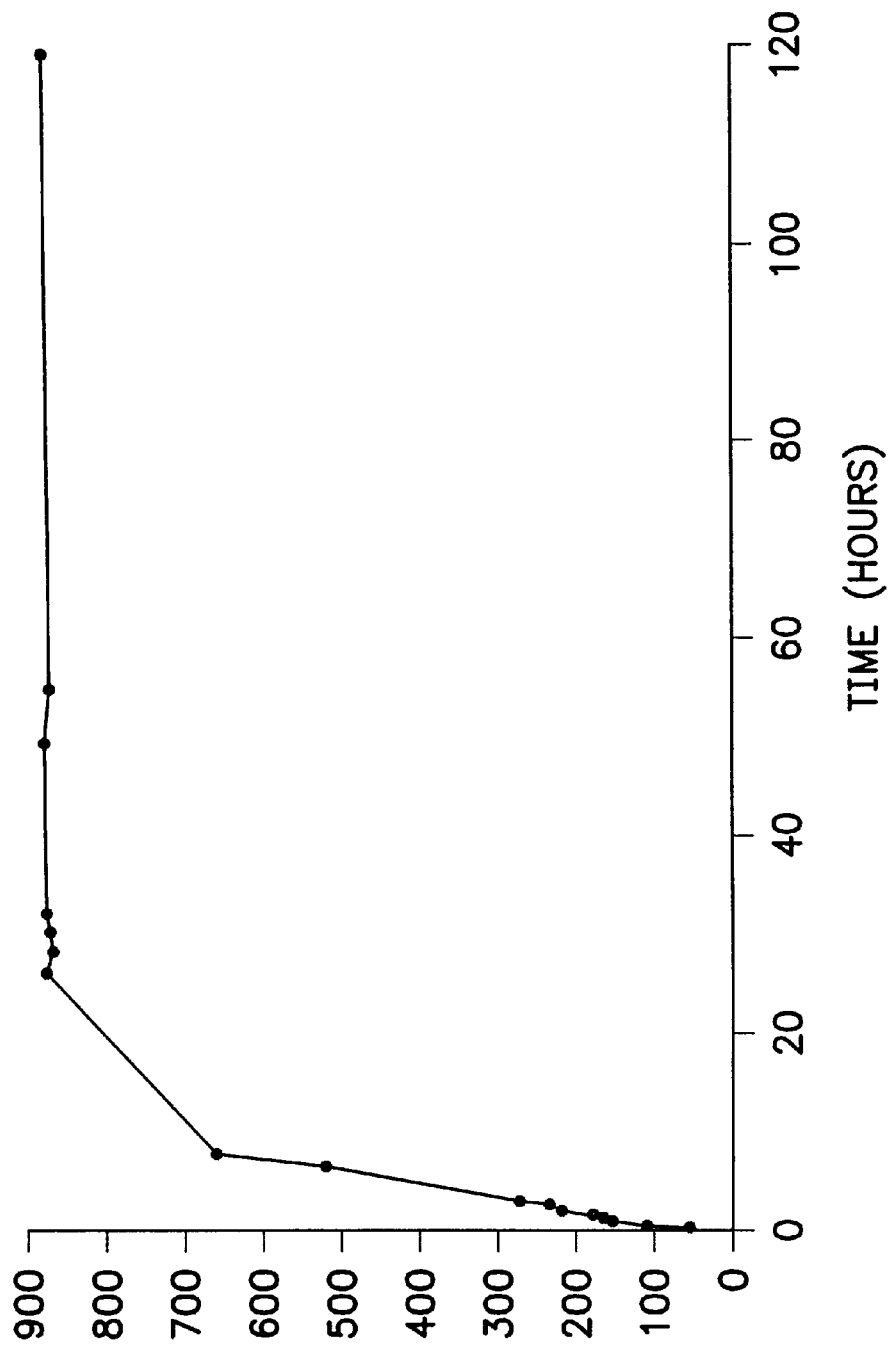
FIG. 4 is a graph illustrating the operation of the electrode illustrated in FIG. 3.

In the construction as already described, an electrode 40 has a hollow bore 46 and a subsequent open cavity 44 which is layered with drug delivery systems offering different rates of response. FIG. 3 illustrates an electrode dipped at the surface 42 in a complex of PEG (polyethylene glycol) 400/dexamethasone sodium phosphate. Within the bore, the same mixture was present and, more rearwardly, within the cavity, a more matrix such as a silicone RTV/dexamethasone sodium phosphate composite was placed for more long term sustained delivery. The composite electrode structure can include many combinations of materials and therapeutics. FIG. 4 depicts an elution rate profile for the composite structure detailed in FIG. 3. Under the conditions of this in vitro study, the PEG 400/dexamethasone complex elutes from the surface and bore over a 24 hour period at which time the silicone RTV/dexamethasone sodium phosphate composite is activated for longer term, slower release.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An implantable cardiac stimulation lead for delivering a tiered drug therapy, comprising:
    an electrically conductive electrode at a distal end of an elongated conductor whose proximal end is adapted to be connected to an implantable stimulation device, the electrode having an exterior surface, an interior cavity, and an axial bore extending between the exterior surface and the interior cavity; and
    a matrix member received within the interior cavity containing a therapeutic drug;
    wherein the exterior surface of the electrode is coated with a wetting agent compounded with the therapeutic drug; and
    wherein the bore is filled with a wetting agent compounded with the therapeutic drug;
    whereby tiered delivery to a recipient of the therapeutic drug is achieved first from the exterior electrode surface, then from the bore, and finally from the matrix member.

2. The lead, as set forth in claim 1, wherein the diameter of the bore is insufficient to allow the intrusion of body fluid from the recipient into the cavity in the absence of a wetting agent.

3. The lead, as set forth in claim 2, wherein the porosity of the exterior surface and of the bore is at least about 0.1% and no greater than about 50%.

4. The lead, as set forth in claim 1, wherein the diameter of the bore is between about 0.001 inches and 0.025 inches.

5. The lead, as set forth in claim 1, wherein the wetting agent is a hydrophilic, water soluble, biocompatible material.

6. The lead, as set forth in claim 1, wherein the opening of the bore at the exterior surface of the electrode is between about 0.1% and 50% of the entire surface area of the electrode.

7. The lead, as set forth in claim 1, wherein the matrix member is composed of silicone rubber.

8. An implantable cardiac stimulation lead comprising:
    an elongated electrical conductor having a proximal end and a distal end;
    an insulative electrical sheath covering the electrical conductor;
    an electrical connector coupled to the proximal end of the electrical conductor and adapted for connection with an implantable stimulation device;
    an electrically conductive electrode at a distal end of an elongated conductor whose proximal end is connected to the electrical pulse generator, the electrode having an exterior surface, an interior cavity, and an axial bore extending between the exterior surface and the interior cavity; and
    a matrix member received within the interior cavity containing a therapeutic drug;
    wherein the exterior surface of the electrode is coated with a wetting agent compounded with the therapeutic drug; and
    wherein the bore is filled with a wetting agent compounded with the therapeutic drug;
    whereby tiered delivery to a recipient of the therapeutic drug is achieved first from the exterior electrode surface, then from the bore, and finally from the matrix member.

9. The lead, as set forth in claim 8, wherein the diameter of the bore is insufficient to allow the intrusion of body fluid from the recipient into the cavity in the absence of a wetting agent.

10. The lead, as set forth in claim 9, wherein the porosity of the exterior surface and of the bore is at least about 0.1% and no greater than about 50%.

11. The lead, as set forth in claim 8, wherein the diameter of the bore is between about 0.001 inches and 0.035 inches.

12. The lead, as set forth in claim 8, wherein the wetting agent is a hydrophilic, water soluble, biocompatible material.

13. The lead, as set forth in claim 8, wherein the opening of the bore at the exterior surface of the electrode is between about 0.1% and 50% of the entire surface area of the electrode.

14. The lead, as set forth in claim 8, wherein the matrix member is composed of silicone rubber.

* * * * *